(12) United States Patent
Song et al.

(10) Patent No.: US 9,703,395 B2
(45) Date of Patent: Jul. 11, 2017

(54) SYSTEM AND METHOD FOR DETECTING INTERPERSONAL TOUCH USING ELECTRICAL PROPERTIES OF SKIN

(71) Applicant: Korea Advanced Institute of Science and Technology, Daejeon (KR)

(72) Inventors: Junehwa Song, Daejeon (KR); Yuhwan Kim, Daejeon (KR); Seungchul Lee, Daejeon (KR); Inseok Hwang, Daejeon (KR); Hyunho Ro, Daejeon (KR); Youngki Lee, Daejeon (KR); Miri Moon, Daejeon (KR)

(73) Assignee: KOREA ADVANCED INSTITUTE OF SCIENCE & TECHNOLOGY (KAIST), Daejeon (KR)

( * ) Notice: Subject to any disclaimer, the term of this patent is extended or adjusted under 35 U.S.C. 154(b) by 205 days.

(21) Appl. No.: 14/666,339

(22) Filed: Mar. 24, 2015

(65) Prior Publication Data
US 2015/0316676 A1   Nov. 5, 2015

(30) Foreign Application Priority Data

Apr. 30, 2014   (KR) .................. 10-2014-0052777

(51) Int. Cl.
*G08B 23/00*   (2006.01)
*G06F 3/0338*   (2013.01)
(Continued)

(52) U.S. Cl.
CPC ....... *G06F 3/0338* (2013.01); *G01R 29/0814* (2013.01); *G01V 3/08* (2013.01);
(Continued)

(58) Field of Classification Search
CPC . G01R 29/0814; H04W 4/003; A61B 5/0531; A61B 5/165; A61B 5/6802; A61B 5/6831; G06F 3/001; G01V 3/08
(Continued)

(56) References Cited

U.S. PATENT DOCUMENTS 3,911,215 A   10/1975   Hurst et al.
8,294,557 B1   10/2012   Saddik et al.
(Continued)

FOREIGN PATENT DOCUMENTS

KR   10-2010-0102605 A   9/2010

OTHER PUBLICATIONS

Nishkam Ravi, Nikhil Dandekar, Preetham Mysore, and Michael L. Littman, Activity Recognition from Accelerometer Data. In Proceedings of the 17th Conference on Innovative Applications of Artificial Intelligence (IAAI '05), 1541-1546, vol. 3, AAAI Press, 2005.

(Continued)

*Primary Examiner* — John A Tweel, Jr.
(74) *Attorney, Agent, or Firm* — Cho-Won IP Consulting; Hyun Ho Song

(57) ABSTRACT

Disclosed herein is an accurate and efficient, yet non-obtrusive system and method (using same) for detecting interpersonal touch, such as a high-five, which is prevalent in people's daily lives, so as to promote everyday interactions at diverse settings. Based on ubiquitous computing technology, one embodiment of the system for detecting interpersonal touch comprises a pre-motion filter for filtering a pre-motion prior to the interpersonal touch, a sensor for sensing electrical properties of skin, an evaluator for analyzing and determining the interpersonal touch based on the pre-motion and the electrical properties of skin, and a (Continued)

communicator for communicating information analyzed by the evaluator. Other embodiments are described and shown.

19 Claims, 6 Drawing Sheets

(51) Int. Cl.
| | |
|---|---|
| G01V 3/08 | (2006.01) |
| G06Q 10/10 | (2012.01) |
| H04W 4/00 | (2009.01) |
| G01R 29/08 | (2006.01) |
| G06F 3/01 | (2006.01) |
| A61B 5/00 | (2006.01) |
| A61B 5/053 | (2006.01) |
| A61B 5/11 | (2006.01) |

(52) U.S. Cl.
CPC .............. *G06F 3/011* (2013.01); *G06F 3/017* (2013.01); *G06Q 10/10* (2013.01); *H04W 4/003* (2013.01); *A61B 5/0531* (2013.01); *A61B 5/1116* (2013.01); *A61B 5/6898* (2013.01)

(58) Field of Classification Search
USPC ...................................................... 340/573.1
See application file for complete search history.

(56) References Cited

U.S. PATENT DOCUMENTS

| | | | |
|---|---|---|---|
| 9,247,903 B2* | 2/2016 | Bender | A61B 5/165 |
| 2014/0203797 A1* | 7/2014 | Stivoric | A61B 5/6804 |
| | | | 324/76.11 |
| 2015/0245164 A1* | 8/2015 | Merrill | H04W 4/06 |
| | | | 370/329 |

OTHER PUBLICATIONS

Munehikio Sato, Ivan Poupyrev, and Chris Harrison, Touché: Enhancing Touch Interaction on Humans, Screens, Liquids, and Everyday Objects, In Proceedings of the SIGCHI Conference on Human Factors in Computing Systems (CHI '12), May 10, 2012, pp. 483-492, Austin, TX, USA.

Tam Vu, Akash Baid, Simon Gao, Marco Gruteser, Richard Howard, Janne Lindqvist, Predrag Spasojevic, Jeffery Walling, Distinguishing Users with Capacitive Touch Communication, In Proceedings of ACM International Conference on Mobile Computing and Networking (MobiCom '12), Aug. 26, 2012, Istanbul, Turkey.

Yuhwan Kim, Seungchul Lee, Inseok Hwang, Hyunho Ro, Youngki Lee, Miri Moon, and Junehwa Song, High5: Promoting Interpersonal Hand-to-Hand Touch for Vibrant Workplace with Electrodermal Sensor Watches, Ubicomp '14, Sep. 17, 2014, Seattle, WA, USA.

* cited by examiner

SYSTEM AND METHOD FOR DETECTING INTERPERSONAL TOUCH USING ELECTRICAL PROPERTIES OF SKIN

BACKGROUND

1. Field of the Invention

The present disclosure relates to a system and method (including same) for detecting interpersonal touch using electrical properties of skin.

2. Description of Related Art

Interpersonal touch is a fundamental, yet often overlooked channel of daily social interactions. Such tactile contact or stimulation provides an effective means of influencing people's social behaviors, while promoting their emotional well-being. As seen, for example, in a romantic relationship, interpersonal touch creates a bond between couples and strengthens their relationship. Likewise in a family relationship, interpersonal touch creates bonds among groups of people.

At workplaces, where people spend a great part of their lives, interpersonal touch may propagate vibrant workplace culture—thereby, boosting social interactions, for example, among coworkers and positively changing their attitude toward one another. A strong handshake, a gentle, encouraging pat on the back by a supervisor, or even a gentle brush of shoulders among coworkers may convey vitality and immediacy often-times more powerful than verbal language. A casual yet cheerful action or motion such as a high-five may also promote diverse social atmosphere and interactions at workplaces.

Despite these significant attributions of interpersonal touch in various facets of everyday life, surprisingly little technical advances have been made in this field. Moreover, there is a wide-spread caution or prohibition often found against or concerning touch-based interactions, especially at workplaces. In this age of ubiquitous computing, an accurate, efficient, yet non-obtrusive way of detecting and utilizing, and thereby promoting interpersonal-touch-based interaction is needed.

BRIEF SUMMARY

According to an embodiment of the present invention, a system for detecting interpersonal touch, may comprise a pre-motion filter for filtering a pre-motion prior to the interpersonal touch, a sensor for sensing electrical properties of skin, an evaluator for analyzing and determining the interpersonal touch based on the pre-motion filtered by the pre-motion filter and the electrical properties of skin sensed by the sensor, and a communicator for communicating data for the interpersonal touch analyzed by the evaluator.

According to an embodiment, the pre-motion filter may comprise an accelerometer, wherein the accelerometer detects a motion in a given part of a body.

According to an embodiment, the electrical properties of skin sensed by the sensor may be SPL (skin-potential level).

According to an embodiment, the evaluator may extract at least one feature for distinguishing and evaluating the electrical properties of skin sensed by the sensor.

According to an embodiment, the feature extracted by the evaluator may comprise at least one of a first derivative, a second derivative, a mean, and a standard deviation, and the feature may be classified using a decision tree.

According to an embodiment, the system for detecting interpersonal touch may be in a wearable computer form.

According to an embodiment of the present invention, a method for detecting interpersonal touch may comprise: filtering a pre-motion prior to the interpersonal touch; sensing electrical properties of skin; analyzing and determining the interpersonal touch based on the pre-motion filtered and the electrical properties of skin sensed; and communicating information of the interpersonal touch analyzed.

According to an embodiment, the filtering the pre-motion prior to the interpersonal touch may be performed by detecting a motion in a given part of a body, using an accelerometer.

According to an embodiment, the electrical properties of skin may be SPL (skin-potential level).

According to an embodiment, the method for detecting interpersonal touch may further comprise extracting at least one feature for distinguishing and evaluating the electrical properties of skin sensed.

According to an embodiment, the feature extracted may comprise at least one of a first derivative, a second derivative, a mean, and a standard deviation, and the feature may be classified using a decision tree.

According to an embodiment, the interpersonal touch may, for example, be a high-five.

According to another embodiment of the present invention, a method for detecting interpersonal touch may comprise: detecting electrical signals of skin and calculating a plurality of electrical-properties features from the electrical signals detected; determining a touch based on the electrical-properties features calculated; identifying and distinguishing the interpersonal touch from the touch; and communicating information associated with the interpersonal touch identified.

According to an embodiment, the identifying and distinguishing the interpersonal touch may be performed by analyzing a signal change caused by change in users' skin potential levels (SPL) or amplitude change in the electrical signals based on noise generated from nearby electrical devices.

According to an embodiment, the electrical-properties features may comprise a size or strength per a given distance of noise generated from nearby electrical devices by which the noise affects the electrical signals.

According to an embodiment, the information associated with the interpersonal touch identified may comprise a person-or-object distinction, identities of persons touched, touch time, and touch duration.

According to an embodiment, the method may be performed by using a program command stored in a computer-readable recording medium.

BRIEF DESCRIPTION OF DRAWINGS

In the accompanying drawings, closely related figures (FIG.'s) have the same number but different alphabetical suffixes.

DETAILED DESCRIPTION

Figure 1:
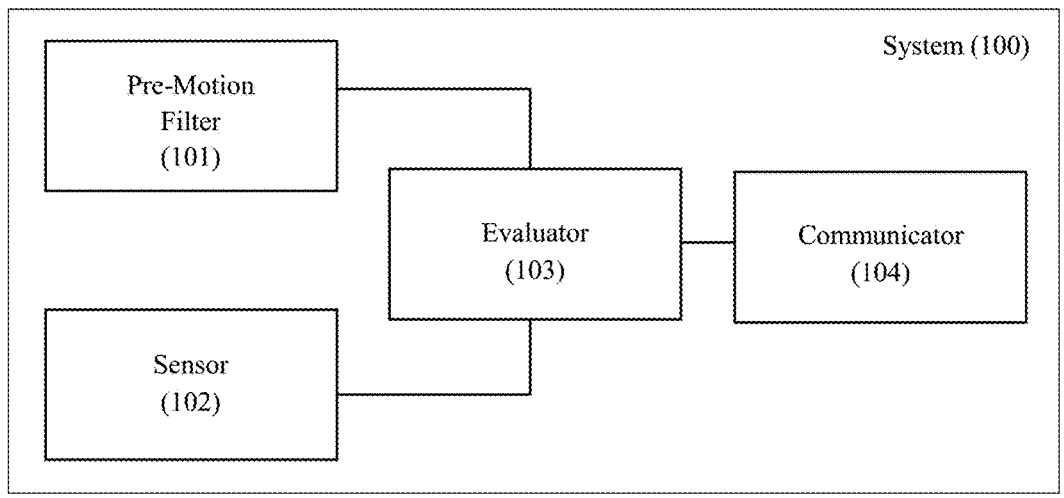
FIG. 1 shows a block diagram of a system for detecting interpersonal touch, according to an embodiment.

According to the present invention, a mobile service including a sensor system and method for detecting interpersonal touch is disclosed to catalyze adaptation of interpersonal touch as a natural organizational meme, for example, to enrich everyday workplace interactions and to promote greetings, encouragement, agreement, etc., among workers. The mobile service (i.e., the sensor system and method) is presented and described in two aspects: (i) application-scenarios, uses, and positive affects brought to workplace setting, as well as analysis and other implications of the mobile service through user-participant research; and (ii) exemplary embodiments of the sensor system and method for detecting interpersonal touch. Performance evaluation of the sensor system and method follows thereafter, with other remarks.

User-Participants Selection and Research:

The mobile service and its affects in various workplace settings with peer-interactions have been studied through a series of systematic research. In one particular case of the research, which is described below, 19 user-participants were recruited from an online community (pool), according to following criteria: the user-participants are employees who (1) work in an office setting, (2) closely interact with others in a workgroup or team with 4 or more members (co-employees), and (3) work at an office with more than 20 employees present.

To ensure coverage of diverse workplaces, each of the 19 user-participants was recruited from different organizations or business entities. To reliably ascertain individual perspective, each of the user-participants recruited had at most 5 years of experience in his/her respective career/field. As supervisors, managers, and executives with their authority over others tend to have and lean toward organizational perspective, these supervisory or managerial user-participants have been studied separately. Table 1 shows a summary of demographics for the user-participants.

TABLE 1

User-Participants Demographics

| ID | Age | Gender (M/F) | Experience (Months) | Workplace/Area | Job/Duty |
|---|---|---|---|---|---|
| P1 | 27 | F | 24 | Education (University) | Administration |
| P2 | 27 | F | 36 | General Hospital | Research |
| P3 | 28 | M | 12 | Appliance (Company) | Software (Engineering) |
| P4 | 29 | M | 6 | Internet Start-up | Web Service |
| P5 | 28 | M | 24 | Mobile Gaming | Software (Engineering) |
| P6 | 28 | M | 3 | Business Consulting | Advertising |
| P7 | 33 | M | 60 | Education (University) | Clerical (Library) |
| P8 | 30 | M | 48 | System Integration | Web Security |
| P9 | 27 | M | 12 | Internet Portal | Software (Engineering) |
| P10 | 28 | F | 24 | Charitable Organization | Administration |
| P11 | 33 | M | 48 | Internet Portal | Software (Engineering) |
| P12 | 31 | M | 12 | Internet Search | Software (Engineering) |
| P13 | 33 | M | 60 | System Integration | Standardization |
| P14 | 34 | M | 60 | IT Consulting | Consulting |
| P15 | 27 | F | 12 | Fashion | Merchandizing |
| P16 | 27 | F | 36 | Stock Trading | Marketing |
| P17 | 30 | M | 48 | Stock Trading | Corporate Finance |
| P18 | 29 | M | 36 | Construction | International Business |
| P19 | 27 | F | 12 | Trading | Translation |

For each of the user-participants, the research included an hour-long semi-structured interview conducted mainly in two phases: (1) to inquire into his/her experience regarding interpersonal touch at workplaces and effort made thereto, to promote a friendly workplace environment; and (2) to collect responses, including both positive and negative expectations and suggestions, based on the mobile service after, for example, showing a video of exemplary application-scenarios. Findings and results of the research are selectively noted below.

The mobile service may have various applications (or uses) and may be modified theretofore, depending on workplace or organizational parameters or needs. Therefore, only a few preliminary and exemplary application-scenarios are described.

Scenario: Checking-in at Work

One morning, Jamie, who works at a software development company, comes into office to work. He says, "Good morning!" and makes a high-five motion to his co-workers. Here, a high-five motion is made as an alternative to an otherwise routine office check-in that has been performed by tagging an ID card at a register. Through a high-five motion, office check-in is re-formed into dynamically interactive and cheerful experience.

Scenario: Earning High-Five Points and Other Incentives

Jamie earns high-five points or other rewards by making a high-five motion with other people at the office. The points may vary depending on a status or identity of the other people. For example, Jamie may earn: 1 point for a high-five motion with an immediate co-worker; 3 points, with a new worker; and 5 points, with an executive or director. Interactions with new personnel and across company hierarchy may thus be encouraged. Jamie redeems accrued points, for example, for a free cup of coffee at a company dining facility.

Research Results and Analysis:

User-participants in the research expressed enthusiasm for such monetary rewards as points-earnings. However, other intangible incentives were found to exist through the mobile service. A great number of the user-participants indicated that the mobile service was a major force in creating a more lively and cheerful atmosphere at their offices—away from otherwise routine and dull morning atmosphere. For example, the user-participants P8 and P9 expressed disapproval for greeting co-workers in the morning with a mere nod or eye contact. Moreover, the user-participants (e.g., P10) indicated that a touch-based praise or complement (coupled with words such as "Good job!") from a supervisor has more profound effects than that with mere words alone—that touch-based praise leads to both workplace productivity and personal psychological well-being for workers in general.

In addition to a functional aspect of the mobile service (e.g., checking-in at work), many of the user-participants also emphasized importance of fun and (personal) satisfaction resulting from use of the mobile service as (personal) motivational force. Still, many others (e.g., P5, P10) indicated that the mobile service facilitates and promotes workplace interactions by initiating basic, yet new workplace exchanges, for example, among non-interactive supervisor and his/her workers, while strengthening many (often-times awkward) pass-by interactions among co-workers, for example, from a different workgroup or team.

Supplementary Study with Executives:

Aside from lower-level workers studied above, user-participants at an executive level have also been recruited to ascertain organizational or company-wide perspective. To illustrate an example of such perspective, a particular executive who was recruited headed a company with numerous workers—but had only 8, a few years earlier. The executive stated, "We [employees at the company] used to have family gatherings and talk to each other [frequently] . . . . Now, one employee recently quit but even his team members don't know exactly why." The executive showed great expectation for the mobile service (in the present invention) to regain family-oriented atmosphere that once existed at the company, but now lost, after the company's rapid growth.

Exemplary Embodiments of Sensor System and Method:

To support, for example, the exemplary application-scenarios discussed above, a sensor system and method for detecting interpersonal touch using electrical properties of skin is described in more detail, hereafter.

FIG. 1 show a block diagram of the sensor system, according to an embodiment. Referring to FIG. 1, the system 100 for detecting interpersonal touch may comprise: a pre-motion filter 101 for detecting and filtering a pre-motion or movement prior to interpersonal touch; a sensor 102 for sensing electric properties of skin (of a user of the system 100); a processor or an evaluator 103 for analyzing and determining interpersonal touch based on the pre-motion filtered by the pre-motion filter 101 and the electrical properties of skin sensed by the sensor 102. The system 100 may further comprise a communicator 104 for communicating data or information of/for interpersonal touch analyzed by the evaluator 103.

Figure 2:
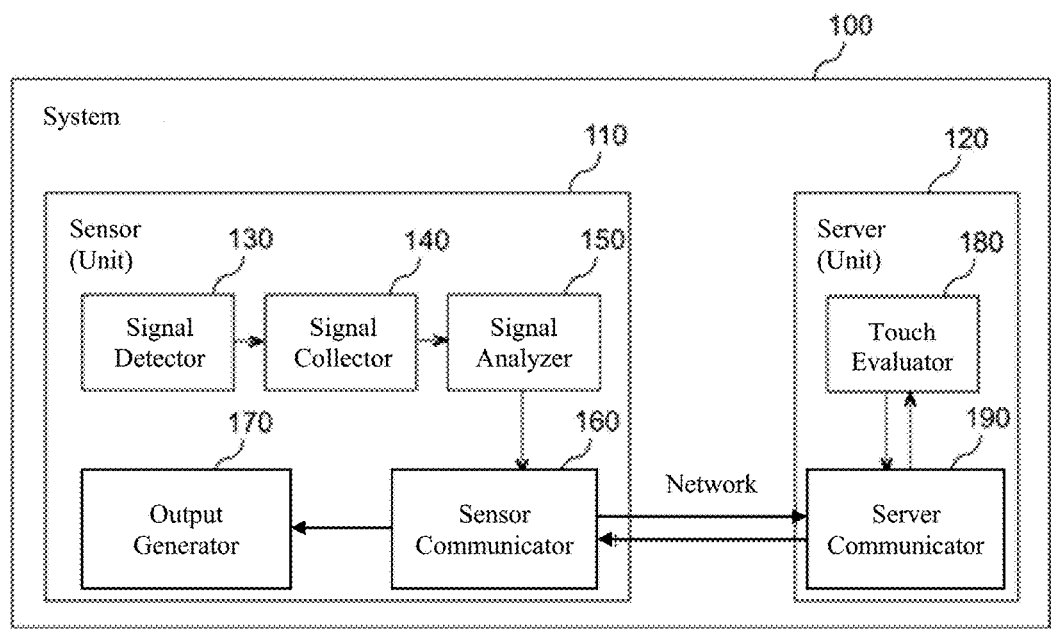
FIG. 2 shows a block diagram of a system for detecting interpersonal touch, according to another embodiment.

FIG. 2 show a block diagram of the sensor system, according to another embodiment. Referring to FIG. 2, the system 100 for detecting interpersonal touch may comprise a sensor (unit) 110 and a server (unit) 120. The sensor unit 110 may comprise a signal detector 130, a signal collector 140, a signal analyzer 150, a sensor communicator 160, and an output generator 170. The server unit 120 may comprise a touch evaluator 180 and a server communicator 190. The system 100 may further comprise a pre-motion filter (not shown) for detecting and filtering a pre-motion or movement prior to interpersonal touch. For example, the sensor unit 110 may further comprise the pre-motion filter.

The signal detector 130 is configured to receive and measure input or electrical signals from skin to detect electrical properties of skin (of a user of the system 100). The signal detector 130 may further comprise an electrode to acquire electrical signals directly from the user (e.g., the user's wrist, neck, etc.) via the electrode attached or placed there-to. The signal detector 130 may also be configured to acquire electrical signals indirectly from the user through the user's clothing or other objects (e.g., belt) via electricity or electrical current conducted or transmitted there-through. The signal detector 130 may further comprise a converter to convert the electrical signals from analog to digital signals.

The signal collector 140 calculates data for detecting touch based on the electrical signals detected or acquired by the signal detector 130. The data may include amplitude, phase, frequency, and various other features of (the) electrical signals, for example, in the digital signals converted the signal detector 130.

The signal analyzer 150 determines an occurrence of touch based on (the) various features of the electrical signals calculated by the signal collector 140. An occurrence of touch may include touch between/among different people and/or objects. For example, the signal analyzer 150 may determine and identify an occurrence of touch based on a change in amplitude of the electrical signals (as) calculated by the signal collector 140. A touch may be determined to have occurred and thus identified, for example, when amplitude in a given (short) time-frame increases or decreases drastically.

The sensor communicator 160 performs and manages data communication between the sensor unit 110 and the server unit 120, for example, via wired/wireless network. When a touch is determined to have occurred and thus identified by the signal analyzer 150, the sensor communicator 160 sends touch event data to the server communicator 190 (operating in the server unit 120). The touch event data may include occurrence time and electrical signal properties for the touch event, as well as system user information (e.g., userid's). The sensor communicator 160 receives touch evaluation data (described later) sent from the server communicator 190 and relays the touch evaluation data to the output generator 170.

The output generator 170 provides touch evaluation data and other touch-related information to various applications supporting detection of interpersonal touch. For example, the output generator 170 may provide such useful information as touch time, duration, and identities as to touching/touched users, as well as person-or-object distinction as to an entity touched.

The touch evaluator 180 (operating in the server unit 120) determines and identifies an occurrence of interpersonal touch (i.e., touch between/among users or people), as well as identities of users involved, based on the touch event data received from other users (e.g., from each respective sensor communicator 160 of the other users' systems 100). For example, the touch evaluator 180 may receive various touch event data within a given time-frame and determine interpersonal touch by analyzing and comparing change in size or strength of (electrical signals) amplitude and extent thereto.

The server communicator 190 (operating in the server unit 120) performs and manages touch-data communication with the sensor communicator 160 in the sensor unit 110, for example, via wired/wireless network. The server communicator 190 may receive the touch event data from the sensor communicator 160. The server communicator 190 may send the touch evaluation data from the touch evaluator 180 to the sensor communicator 160.

Figure 3:
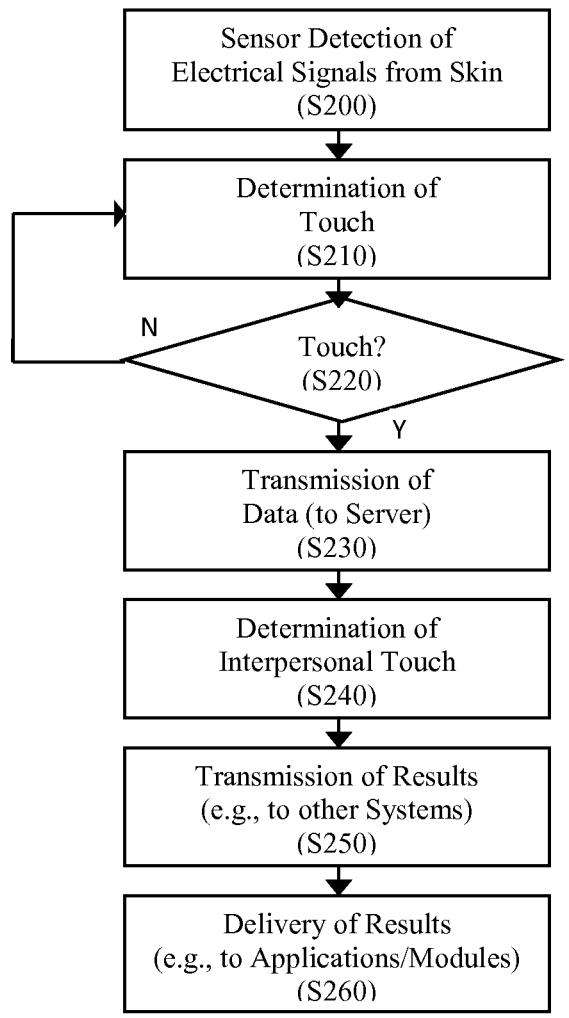
FIG. 3 shows a flowchart for a method for detecting interpersonal touch using electrical properties of skin of a user and other user-acquired information, according to an embodiment.

FIG. 3 shows a flowchart for a method for detecting interpersonal touch using electrical properties of skin of a user (and other user-acquired information), according to an embodiment. The method is described later.

Interpersonal touch may be a common action or motion such as a high-five or a handshake, but is not limited thereto. The system and method therein are not limited to or dependent on such type of action or motion. Use of the high-five motion herein is merely exemplary and correlates mainly to the user-participant research (described earlier) and the performance evaluation of the sensor system and method (described later), where a high-five motion was used for testing purpose.

Figure 4:
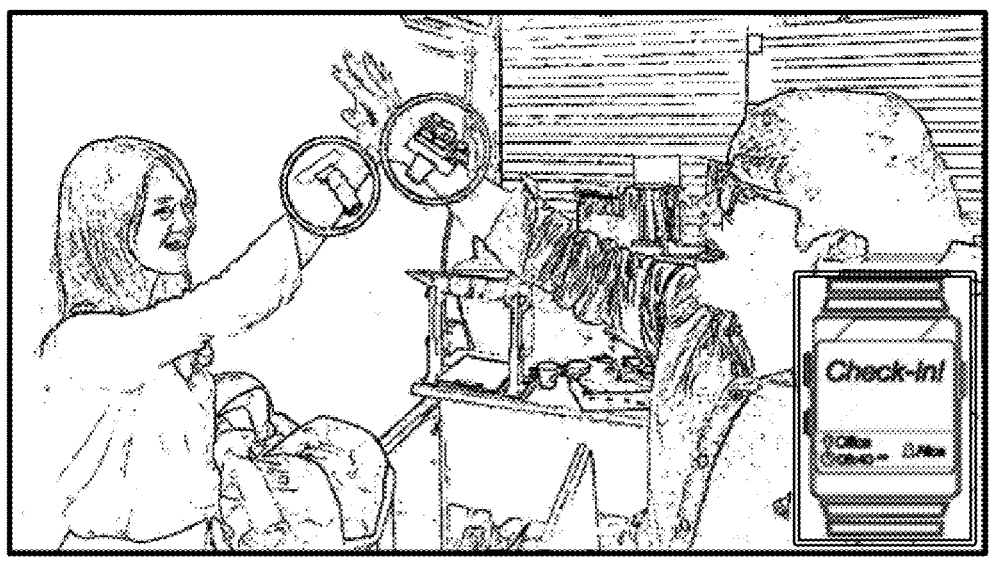
FIG. 4 shows two users making a high-five motion while (each user is) wearing a system for detecting interpersonal touch—with a lower-right side inset in FIG. 4 showing a mobile application—both, according to an embodiment.

FIG. 4 shows two users (user-participants) making a high-five motion while (each user is) wearing the sensor system for detecting interpersonal touch, according to an embodiment. A lower-right side inset in FIG. 4 shows an embodiment of a mobile application for the system. Referring to FIG. 4, the system may be in watch-style (e.g., smartwatch) form but is not limited thereto; the system may be in other mobile or wearable forms (e.g., necklace, earring, bracelet, armband, etc.). Hence, the system detects interpersonal touch in a practical, non-cumbersome, and non-obtrusive, yet efficient way.

Figure 5A:
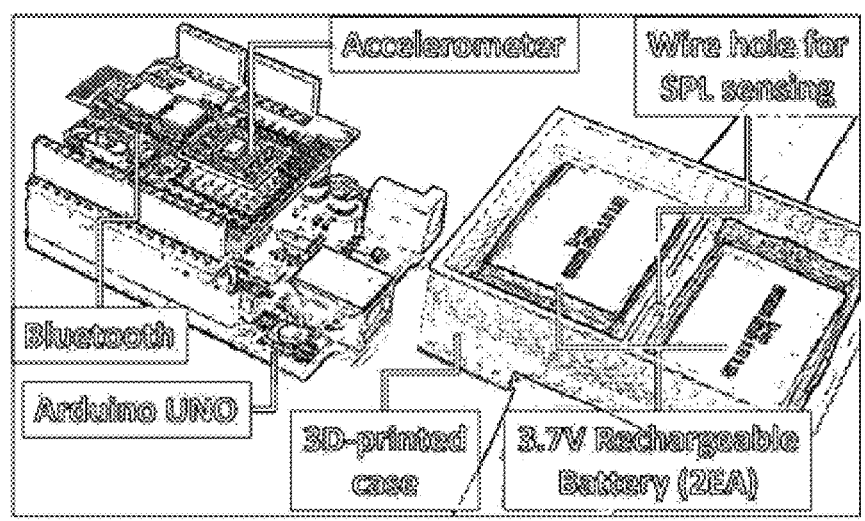
FIG. 5A shows a system for detecting interpersonal touch in a user-wearable form, according to an embodiment.
Figure 5B:
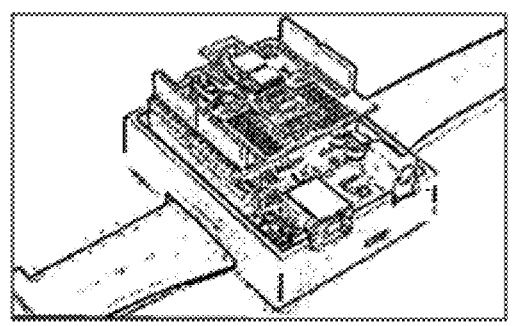
FIG. 5B shows partial circuitry in(side) the system, according to an embodiment.
Figure 5C:
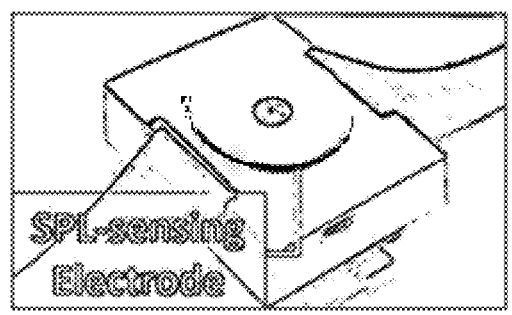
FIG. 5C shows a skin potential level (SPL) sensing electrode on an underside of the system, according to an embodiment.

FIG. 5A shows the sensor system for detecting interpersonal touch in a user-wearable, watch-style form according to an embodiment. FIG. 5B shows a circuitry in(side) the system (without a top case or cover), according to the embodiment in FIG. 5A. FIG. 5C shows an SPL-sensing electrode on an underside of the system according to the embodiment in FIG. 5A.

Referring to FIG.'s 5A-5C, the system may include a small electrode to sense and capture the skin potential level (SPL). The system may detect and capture naturally occurring SPL (of an outer wrist) of a system user when the electrode comes in contact with skin on the outer wrist of the user. SPL may represent endosomatic voltage levels, and the SPL may change upon touching or coming into contact with, for example, skin or various other surfaces of (conductive) material. SPL may also be affected, for example, by biological conditions, such as muscular motions and perspirations.

Different from SCL (or Skin Conductance Level), SPL may be passively sensed or measured, for example, without applying external (electrical) current on the skin. Thus, while the electrode may be in prolonged contact with a system user's skin, a possible concern for safety of the user is resolved (even for the skin that may be wet or perspiring). Moreover, as shown in FIG. 5C, the system in a watch-style form may inconspicuously or unobtrusively detect and capture SPL of the user as the small electrode is on an underside of the system, wherein the small electrode comes (naturally or directly) in contact with the outer wrist of the user.

Figure 6:
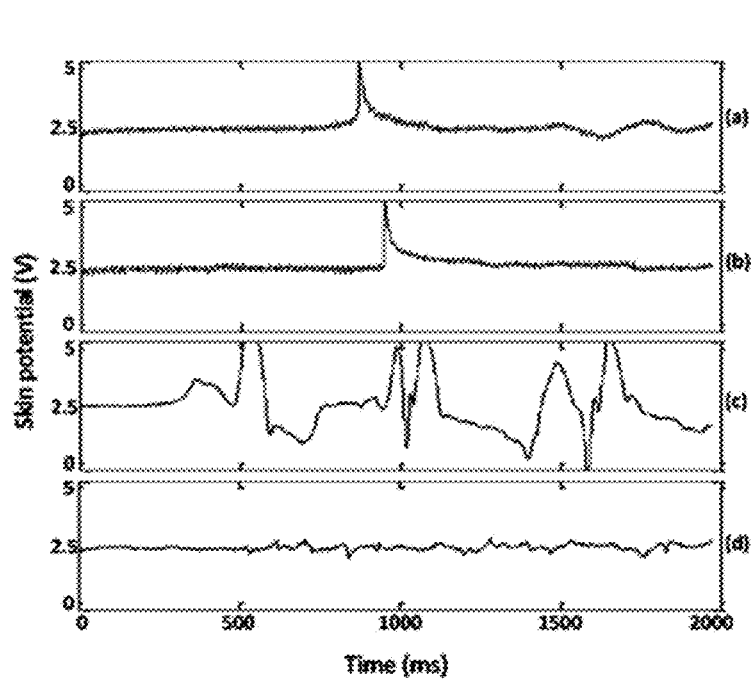
FIG. 6 shows a graph of skin potential level (SPL) readings for each motion of/for (a) high-five, (b) handshake, (c) walking, and (d) keyboard typing.

FIG. 6 shows a graph of skin potential level (SPL) readings for each motion of/for (a) high-five, (b) handshake, (c) walking, and (d) keyboard typing. Referring to FIG. 6, the SPL readings show a sharp peak at a point when a hand (of one system user) comes in contact with another hand (of another system user) during each of (a) high-five or (b) handshake motions. These sharp, unique peaks in the SPL readings measured during interpersonal-touch-based motions are computationally distinguishable, unlike in the SPL readings measured during non-interpersonal-touch-based motions. FIG. 6 shows clearly different SPL readings, for example, for such daily, non-touch-based or non-interpersonal-touch-based motions as (c) walking or (d) keyboard typing, respectively.

Of significance is accurately distinguishing one interpersonal-touch-based motion from another, which may incur similar SPL readings or patterns.

As described with reference to FIG. 1, the system may comprise the pre-motion filter (101) to detect and filter (out) in a pre-motion stage, other motions, for example, with similar peak patterns in SPL readings, which may (potentially) generate a false-positive output. A pre-motion of/for a high-five motion may involve system users (quickly) raising forearms/arms prior to clapping of their hands. This pre-motion may be unique and thus, distinguishable from (those of) other touch-based or interpersonal-touch-based actions or motions, such as a handshake. In one embodiment (e.g., shown in FIG. 4), the system may further comprise an accelerometer (not shown) to accurately and efficiently detect the pre-motion. The accelerometer may provide motion data for simple linear acceleration. Pre-motion filtering and SPL sensing for SPL readings and analyses are described in more detail below.

Stage 1: Pre-Motion Filtering

To filter out other touch-based actions or motions, which may show similar patterns in SPL reading to those of, for example, a high-five motion, simple but effective accelerometer-augmented heuristics may be performed. Accelerometer data may be sampled at a given frequency and windowed in a given time frame. The data may (then) be evaluated to check if/whether an axis (e.g., "y-axis"), which is parallel to an arm (in a pre-motion) of a system user, quickly rises toward an axis of gravity. The given time period may, for example, be two seconds, and the rate of sampling may, for example, be 120 Hz. Pre-motion filtering may run as an always-running front-end service, which may need to operate in a highly efficient manner: this simple accelerometer-augmented heuristics provide such high efficiency (e.g., simple design with negligible power consumption).

Stage 2: SPL-Based Identification

When the pre-motion of the high-five motion is detected, SPL sensing (by the sensor 102) is initiated to check if/whether the high-five motion (including the clapping of hands or a contact) actually follows the pre-motion. Conventional or standard techniques may be applied on the SPL readings to identify (the) unique peaks associated with the high-five motion. SPL data may be collected, for example, at 2 kHz and windowed, for example, for 2 seconds. To identify the peaks, one or more of such features as 1st and 2nd order derivatives, (their) mean(s), and standard deviations may be extracted from the data. The features may then be classified using a decision tree (e.g., J.48). Once the high-five motion is detected and verified, identifying or identification information analyzed (by the evaluator 103) may be communicated (by the communicator 104) to and exchanged among system users. System applications may also be notified for additional user-group- or organization-specific processing according to organizational parameters or needs.

Hereafter, a method for detecting interpersonal touch using electrical properties of skin, according to an embodiment, is described in more detail.

FIG. 3 shows a flowchart for a method for detecting interpersonal touch using electrical properties of skin of a system user (and other user-acquired information), according to an embodiment.

Referring to FIG. 3, the method for detecting interpersonal touch may comprise: a step of detecting and measuring electrical signals from skin of a system user (200); a step of determining touch (210); a step of identifying actual touch (220); a step of determining interpersonal touch (240); a step of generating and sending output/results to each user's (other) system (250); and a step of providing results to various modules and applications supporting the system (260). The method for detecting interpersonal touch may further comprise a step of sending associated data to a server (230), after the step (220).

In step (200), electrical signals of/from skin are detected and measured, for example, via an electrode attached to the skin of the user. The electrical signals of skin may include electromagnetic noise in a surrounding area acting on or otherwise affecting the skin and electrostatic signals generated when skin comes in contact with a conductive material. After the electrical signals are detected (e.g., by the signal detector 130), the electric signals may be converted from analog to digital form via an analog-to-digital converter. The converted signals are then sent, for example, to various applications and modules, and amplitude, phase, frequency, and other features of (the) electrical signals are calculated and analyzed to determine and identify person-to-person or person-to-object touch. As the electrical signals of skin may include electromagnetic noise, a size or strength, as well as difference thereof, of various noise from nearby electrical/electronic devices (e.g., per a given distance from the system) may also be the features of the electrical signals.

In step (210), an occurrence of touch is determined based on the features of the electrical signals analyzed in step (200) of detecting electrical signals. The touch is not limited to a person-to-person or interpersonal touch but may also be person-to-object touch including touch between a person/user and any conductive material, such as an electrical device, drinking cup, and door handle.

As partly discussed earlier, two unique changes, among others, may occur in the electrical signals detected from skin when skin touches or otherwise comes in contact with conductive material.

Figure 7:
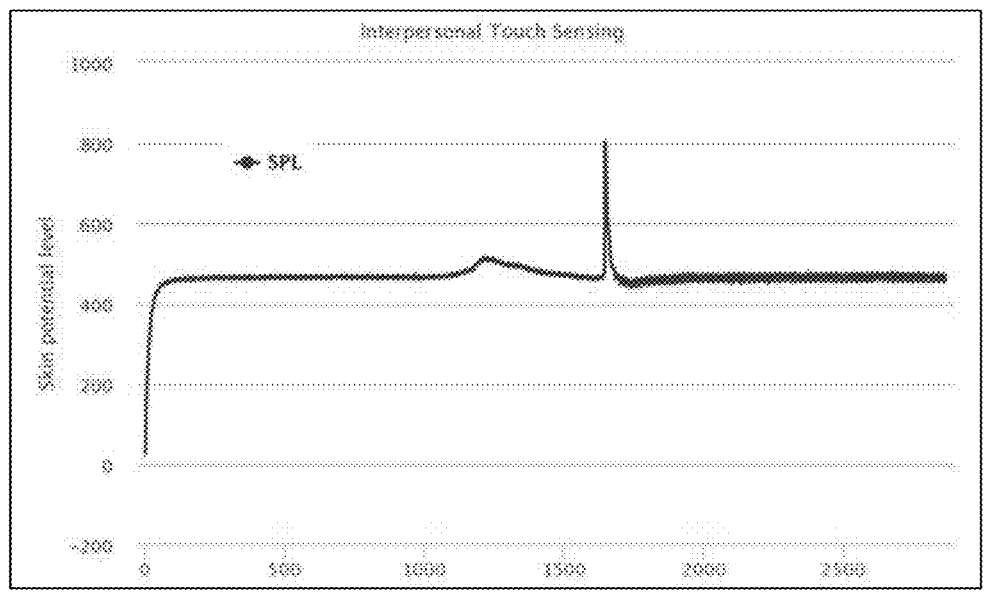
FIG. 7 shows a graph of skin potential level (SPL) readings with a peak indicating interpersonal touch.
Figure 8:
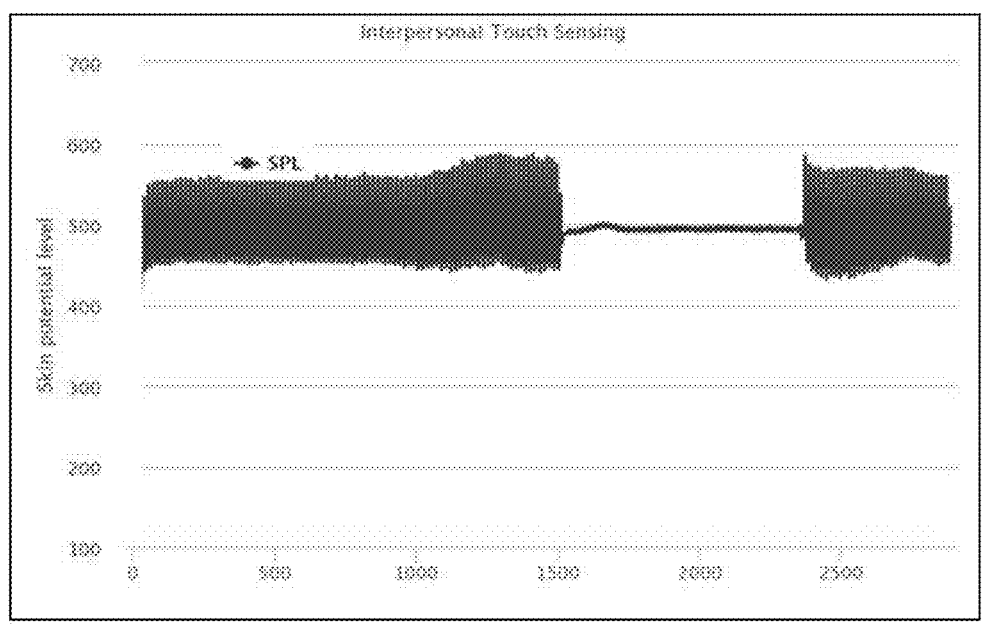
FIG. 8 shows a graph of skin potential level (SPL) readings with an amplitude change indicating interpersonal touch.

FIG. 7 shows a graph of electrical signals or skin potential level (SPL) readings with a peak indicating interpersonal touch. FIG. 8 shows a graph of electrical signals or skin potential level (SPL) readings with an amplitude change indicating interpersonal touch.

As shown in FIG. 7, electrostatic signals generated may cause a drastic change in the electrical signals and produce a sharp peak in electrical signals readings. And as shown in FIG. 8, amplitude of the electrical signals may change (e.g., increases or decreases) where skin and a conductive material touched function as one antenna. The two changes may not be exclusive; they may occur simultaneously.

Various calculation techniques may be applied to detect the changes in the electrical signals. To detect a drastic change in the electrical signals caused by electrostatic signals (or by an instant change cause by different skin potential level (SPL) among users), for example, as shown in FIG. 7, a difference may be taken of values measured at times t and t−1, and when the difference exceeds a given threshold, the difference and the (associated) values may be further calculated to detect electrostatic signals generated. To detect amplitude change, for example, as shown in FIG. 8, a difference between/among signal peaks may be calculated and amplitude determined via peak-detection algorithms. The electrical signals may be segmented into a given window size, and such values as standard deviation may be calculated for each window, and amplitude change may be determined based on a change in such values. In step (220), these techniques may be used to determine and identify an actual occurrence of touch between a person/user and any conductive material.

When a touch is actually identified in step (220), associated data is sent in step (230), for example, to a server to further evaluate and distinguish the touch as person-to-person (interpersonal) or person-to-object touch. The data sent, for example, to the server unit 120 may include user (identifying) information, time information (e.g., signal detection time), and various other features of the electrical signals converted or calculated in the step (200) of determining an occurrence of touch.

In step (240), an occurrence of interpersonal touch, as well as identities of the users involved, is evaluated based on the data sent (from each user's system for detecting interpersonal touch). Where two users touch each other, the signal change and the amplitude change as described earlier in step (210) may occur simultaneously. Changes in the signals sent from other users (e.g., from a plurality of other systems) may be compared and analyzed, for example, based on signal-changing time and associated information, and users with signal changes within a given time frame (e.g., within 1 second) may be searched for. Where a user touches an object, no signal with a change may exist at this signal-changing time, and the touch may thus be determined as a non-interpersonal or user-object touch.

In step (250), results in step (240) are sent to each user's system. The results may be sent, for example, by the server communicator 190 only to the sensor unit(s) 110 in the system(s), which have sent the electrical signals.

In step (260), the results sent from the server (e.g., the server unit 120) are delivered to various applications supporting the system. The results may be transmitted, for example, by the output generator 170 by generating system notification to the applications or by providing relevant data upon request by the applications.

Performance Evaluation:

For a performance evaluation of the sensor system and method for detecting interpersonal touch, a number of office workers have been recruited. In one particular case of the evaluation, which is described below, three employees were asked to make (the) high-five motion(s) and also perform nine other, common office work activities, 50 times per each of the motions and the activities. The office work activities were performed under ordinary office settings and included actions or motions of handshaking, hand writing, keyboard typing, grabbing and using phones for calls, using kitchen utensils (e.g., spoon), arm-stretching, and walking Of data collected during the evaluation, 60% was used to train a testing-algorithm, and remaining 40%, for actual testing (using the algorithm). Results from the particular case of the evaluation are detailed in part, below.

First, accuracy of the pre-motion filter and filtering is evaluated. Table 2 shows a confusion matrix of the accuracy of the pre-motion filter (101) in Stage 1. As shown in Table 2, the pre-motion filter (101) detected and filtered 100% of (the) pre-motions for the high-five motions. The pre-motion filter (101) did not filter (out) some pre-motions for non-high-five motions; however, this may be corrected—and the accuracy improved—simply by adjusting system parameters (e.g., fine-tuning threshold-settings in the system 100 or the pre-motion filter 101). Regardless and significantly, the motions, which passed (through) the Stage 1, do not include those motions involving interpersonal touch, which may (potentially) generate false positive output in the SPL-based identification in (the) Stage 2.

TABLE 2

Confusion Matrix for Stage 1

| Confusion Matrix (Stage 1) | | Predicted | |
|---|---|---|---|
| | | High-Five Pre-Motion | Non-High-Five Pre-Motion |
| Actual | High-Five Pre-Motion | 60 (100%) | 0 (0%) |
| | Non-High-Five Pre-Motion | 148 (27.4%) | 392 (72.6%) |

Next, accuracy of the SPL-based identification is evaluated for the motions, which passed the Stage 1 (i.e., 60 high-five and 148 non-high-five motions). Table 3 shows a confusion matrix of the accuracy of the SPL-based identification. As shown in Table 3, the decision tree effectively filtered out the non-high-five motions. Of the features extracted to identify the unique peaks associated with the high-five motion, the 2nd-order derivative had a highest information gain in distinguishing or discriminating the high-five motions. Evidently, in the one particular case of the evaluation described above, the sensor system achieved performance rate of 87.3% for precision and 91.7% for recall for end-to-end detection and filtering for the high-five motions.

TABLE 3

Confusion Matrix for Stage 2

| Confusion Matrix (Stage 2) | | Predicted | |
|---|---|---|---|
| | | High-Five | Non-High-Five |
| Actual | High-Five | 55 (91.7%) | 5 (8.3%) |
| | Non-High-Five | 8 (5.4%) | 140 (94.6%) |

Other Remarks:

Aside from promoting a new meme of interpersonal interaction toward a vibrant group-life culture, the sensor system may find wide application and value in mobile and other ubicomp-technology-based interpersonal or group sensing systems. The system may inspire and lead current social-intervention systems to advance to a next-generation design phase beyond mere verbal interaction. Moreover, with overwhelming importance placed on touch-based interaction(s) for children, the system, according to the present invention, is expected to play a key role in family life and child development. The system may be applied to players of outdoor-game applications (e.g., a digitalized game of "tag"), to thereby greatly enhance children's gaming experience. More still, the system may incorporate a user's impression or mood and make other important contributions to social science—thereby further enriching people's lives, both culturally and technologically.

Exemplary embodiments have been described in detail with references to the accompanying drawings, for illustrative purposes (and) to solve technical problems. Although the description above contains much specificity, these should not be construed as limiting the scope of the exemplary embodiments. The exemplary embodiments may be modified and implemented in various forms and should not be interpreted as thus limited.

A person skilled in the art will understand that various modifications and alterations may be made without departing from the spirit and scope of the description and that such modifications and alterations are within the scope of the accompanying claims.

What is claimed is:

1. A system for detecting interpersonal touch, comprising:
   a pre-motion filter for filtering a pre-motion prior to the interpersonal touch,
   a sensor for sensing electrical properties of skin,
   an evaluator for analyzing and determining the interpersonal touch based on the pre-motion filtered by the pre-motion filter and the electrical properties of skin sensed by the sensor, and
   a communicator for communicating data for the interpersonal touch analyzed by the evaluator.

2. The system for detecting interpersonal touch according to claim 1, wherein the pre-motion filter comprises an accelerometer, wherein the accelerometer detects a motion in a given part of a body.

3. The system for detecting interpersonal touch according to claim 1, wherein the electrical properties of skin sensed by the sensor is SPL (skin-potential level).

4. The system for detecting interpersonal touch according to claim 1, wherein the evaluator extracts at least one feature for distinguishing and evaluating the electrical properties of skin sensed by the sensor.

5. The system for detecting interpersonal touch according to claim 4, wherein:
   the feature extracted by the evaluator comprises at least one of a first derivative, a second derivative, a mean, and a standard deviation, and
   the feature is classified using a decision tree.

6. The system for detecting interpersonal touch according to claim 5, wherein the interpersonal touch is a high-five.

7. The system for detecting interpersonal touch according to claim 1, wherein the system is in a wearable computer form.

8. A method for detecting interpersonal touch, comprising:
   filtering a pre-motion prior to the interpersonal touch;
   sensing electrical properties of skin;
   analyzing and determining the interpersonal touch based on the pre-motion filtered and the electrical properties of skin sensed; and
   communicating information of the interpersonal touch analyzed.

9. The method for detecting interpersonal touch according to claim 8, wherein the filtering the pre-motion prior to the interpersonal touch is performed by detecting a motion in a given part of a body, using an accelerometer.

10. The method for detecting interpersonal touch according to claim 8, wherein the electrical properties of skin is SPL (skin-potential level).

11. The method for detecting interpersonal touch according to claim 8, further comprising
    extracting at least one feature for distinguishing and evaluating the electrical properties of skin sensed.

12. The method for detecting interpersonal touch according to claim 11, wherein:
    the feature extracted comprises at least one of a first derivative, a second derivative, a mean, and a standard deviation, and
    the feature is classified using a decision tree.

13. The method for detecting interpersonal touch according to claim 12, wherein the interpersonal touch is a high-five.

14. The method for detecting interpersonal touch according to claim 12, wherein the method is performed by using a program command stored in a computer-readable recording medium.

15. A method for detecting interpersonal touch, comprising:
   detecting electrical signals of skin and calculating a plurality of electrical-properties features from the electrical signals detected;
   determining a touch based on the electrical-properties features calculated;
   identifying and distinguishing the interpersonal touch from the touch; and
   communicating information associated with the interpersonal touch identified.

16. The method for detecting interpersonal touch according to claim 15, wherein the identifying and distinguishing the interpersonal touch is performed by analyzing a signal change caused by change in users' skin potential levels (SPL) or amplitude change in the electrical signals based on noise generated from nearby electrical devices.

17. The method for detecting interpersonal touch according to claim 15, wherein the electrical-properties features comprise a size or strength per a given distance of noise generated from nearby electrical devices by which the noise affects the electrical signals.

18. The method for detecting interpersonal touch according to claim 15, wherein the information associated with the interpersonal touch identified comprises a person-or-object distinction, identities of persons touched, touch time, and touch duration.

19. The method for detecting interpersonal touch according to claim 15, wherein the method is performed by using a program command stored in a computer-readable recording medium.

* * * * *